United States Patent [19]

Francis et al.

[11] Patent Number: 5,578,295
[45] Date of Patent: Nov. 26, 1996

[54] ORAL CARE COMPOSITIONS COMPRISING CERTAIN SUBSTITUTED DIPHENYL ETHERS

[75] Inventors: Marion D. Francis, Cincinnati; Dennis G. A. Nelson, West Chester, both of Ohio

[73] Assignee: The Procter & Gamble Company, Cincinnati, Ohio

[21] Appl. No.: 431,381

[22] Filed: Apr. 28, 1995

[51] Int. Cl.$^6$ ............................................. A61K 7/16
[52] U.S. Cl. ................................. 424/57; 424/49
[58] Field of Search ......................... 424/49–55, 422

[56] References Cited

U.S. PATENT DOCUMENTS

| | | | |
|---|---|---|---|
| 3,549,662 | 12/1970 | Imai et al. | 260/345.5 |
| 3,629,477 | 12/1971 | Model et al. | 424/340 |
| 4,894,220 | 1/1990 | Nabi | 426/52 |
| 4,980,153 | 12/1990 | Jackson et al. | 424/52 |

FOREIGN PATENT DOCUMENTS

| | | |
|---|---|---|
| 0961412 | 1/1975 | Canada . |
| 0161899 | 11/1985 | European Pat. Off. ......... A61K 7/16 |
| 0278744 | 8/1988 | European Pat. Off. . |
| 2-1402 | 1/1990 | Japan . |
| 1592011 | 7/1981 | United Kingdom . |

OTHER PUBLICATIONS

Kamat, J. Ind. Dent. Asso. 50, 171–175 (1978.
Science vol. 253, Sep. 6, 1991. 1095–96 Miller.
Noguchi. Chem Absts 84, 1976, #135297g.
Miglani, D. C., E. Raghupathy, A. Rajasekher and S. Shyamala, "Studies on Salivary Phosphatases III. On the Possible Relation Between Salivary Alkaline Phosphatase Activity and Gingival Inflammation," J. Periodontol, Jul. 1974, 45(7), 511–13.
Kamat, N. V., "Biochemical Aspects of Periodontal Diseases: II, The Possible Significance of Calcium Phosphorous and Alkaline Phosphatase in Human Saliva," Journal Indian Dent. Asso. 50, 171–175, 1978 (month not known).
Saxton, C. A., B. Svatun and A. M. Lloyd, "Antiplaque Effects and Mode of Action of a Combination of Zinc Citrate and a Nonionic Antimicrobial Agent", Scand. J. Dent. Res, Jun. 1988, 96:212–7.
Jenkins, S., M. Addy and R. Newcombe, "Studies on the Effect of Toothpaste on Plaque Regrowth, (II). Triclosan With & Without Zinc Citrate Formulations," J. Clin. Periodontol, Jul. 1989, 16(6), 385–7 (Eng).
"A Better Way to Make the Medicine Go Down" Research News, Science, vol. 253, Sep. 6, 1991, pp. 1095–1096.
Jenkins, S., M. Addy and R. Newcombe, "Triclosan and Sodium Lauryl Sulphate Mouthrinses (II). Effects of 4–Day Plaque Regrowth," J. Clin. Periodontol Feb. 1991; 18: 145–48.
Marsh, P. D., "Dentrifices Containing New Agents For the Control of Plaque and Gingivitis: Miscrobiological Aspects," J. Clin. Periodontol, Jul. 1991, 18:462–67.
Lindhe, J., "Triclosan/copolymer/fluoride dentifrices: A new technology for the prevention of plaque, calculus, gingivitis and caries", Am. J. Dent., 3:S1–S72 (Sep. 1990).
Van der Ouderaa, F. J. and Cummins, D., "Delivery Systems for Agents in Supra– and Sub–gingival Control", J. Dent. Res., 68:1617–24 (Nov. 1989).

*Primary Examiner*—Gollamudi S. Kishore
*Attorney, Agent, or Firm*—Milton B. Graff; Jean R. Crosman; Betty J. Zea

[57] ABSTRACT

The subject invention encompasses methods and compositions comprising phosphate derivatives of triclosan for treating or preventing dental plaque, gingivitis or periodontal disease, of the oral cavity in humans or lower animals.

22 Claims, No Drawings

ORAL CARE COMPOSITIONS COMPRISING CERTAIN SUBSTITUTED DIPHENYL ETHERS

TECHNICAL FIELD

The subject invention relates to oral compositions, such as dentifrices and oral solutions, designed to treat or prevent dental plaque, gingivitis or periodontal disease.

BACKGROUND OF THE INVENTION

The mouth is a habitat for microbial growth and colonization. Within the mouth, the gums, lips, oral mucosa (cheek), palate, tongue and teeth provide surfaces for the colonization and accumulation of bacteria. Teeth are unique in the oral cavity because they have hard, non-shedding surfaces where bacteria and their products (dental plaque) can significantly accumulate, especially in approximal areas and along the gingival crevice.

Dental plaque is a rough sticky film on the teeth that is made up of saliva, bacteria and food particles which adheres tenaciously to teeth at points of irregularity or discontinuity. Within a few hours of teeth cleaning, a film of salivary mucus, consisting primarily of proteins, forms on the teeth. Various oral bacteria colonize the mucus and multiply, forming a layer of plaque. Carbohydrate food debris adheres to the mucus and is digested by some types of plaque-causing bacteria. The digestion produces both by-products which add to the plaque and acid which erodes tooth enamel.

The oral bacteria in dental plaque includes many gram positive and gram negative microorganisms embedded in an extracellular matrix of insoluble polysaccharides, firmly attached to teeth and other oral surfaces. The colonization of bacteria to form dental plaque follows an ecological pattern where a few pioneer aerobic species, mostly gram-positive streptococci, colonize enamel surfaces. The plaque then progresses through stages of increasing microbial complexity. Mature plaques, often found in protected regions of the teeth, such as cracks, approximal regions and in the gingival crevice, typically contain anaerobes. Saliva and crevicular fluid are a source of nutrients for the dental plaque. Local conditions affect the metabolic activity and composition of dental plaque.

To inhibit the growth of dental plaque, cationic antimicrobial agents have been used in some known oral compositions. However, their performance may be seriously compromised when used with anionic components, such as surfactants, fluoride and pyrophosphate, or the silica abrasives commonly found in dentifrices. Another antiplaque agent, the zinc cation, most often delivered as the relatively insoluble zinc citrate trihydrate salt, can be formulated into dentifrices but only provides a slight inhibitory effect on plaque formation.

Nonionic antibacterial agents have also been used in oral compositions. Such agents include phenols, such as thymol and eucalytol; halogenated salicylanilides; and halogenated hyroxydiphenyl ethers, such as triclosan.

Triclosan is a particularly attractive nonionic antibacterial because it is compatible with dentifrice components and has a broad antimicrobial spectrum with no sign that long-term use produces triclosan-resistant bacterial strains (Marsh, P.D., *Dentifrices Containing New Agents for the Control of Plaque and Gingivitis: Microbiological Aspects.* J. Clin. Periodontol. 18:462–67 (1991)). Triclosan has been shown to inhibit Gram-negative gingivitis pathogenic bacteria selectively, and to reduce the ratio of anaerobic to aerobic bacteria (Marsh, 1991 ). However, triclosan's major drawback is its limited water solubility (1 ppm in distilled water at 20° C.). In light of this drawback, previous disclosures have focused on delivering triclosan to the oral cavity in an optimal fashion.

The efficacy of many antimicrobials is greatly influenced by their substantivity in the oral cavity. Each antibacterial has a concentration below which it exhibits little or no activity and less substantive antimicrobials have steeper decay curves. Generally, the longer the antimicrobial's concentration remains above that concentration needed for bacteriocidal activity, the more effective is the antimicrobial.

The substantivity of triclosan is complicated by its poor aqueous solubility. In previous disclosures, triclosan is emulsified by a surfactant in dentifrice to form lameliar, micellar or other surfactant phases. Upon dilution in the mouth, the concentration of surfactant, within a few minutes, falls below the critical micelle concentration (CHC) for a dentifrice surfactant (typically sodium dodecyl sulphate (CMC=0.23%)) and triclosan is precipitated. The precipitated triclosan would probably be biologically inactive and be removed from the oral cavity by ingestion or expectoration.

One disclosed method to improve delivery of triclosan to the oral cavity is to incorporate a lipophilic copolymer of methoxyethylene and maleic acid which enhances the delivery and retention of triclosan on teeth and oral soft tissues (U.S. Pat. No. 4,894,220, Nabi et al., issued Jan. 16, 1990) (c.f. Am. J. Dent. 3:S1–S72 (1990)). This reference discloses triclosan solubilized in the propylene glycol used as a humectant in the dentifrice formulation.

Another method of utilizing triclosan is in combination with zinc citrate trihydrate (Lane et al., Eur. Pat. Appl. No. 0,161,899 published Nov. 21, 1985). The combination of zinc citrate trihydrate and triclosan has been reported to have an additive effect on anti-plaque and anti-gingivitis activity. Eur. Pat. Appl. No. 0,161,899 discloses dentifrices in which zinc induces a lamellar surfactant phase with triclosan and the sodium dodecyl sulphate surfactant. This solubilizes the triclosan and helps deliver the antimicrobial to the plaque. It has been suggested that there is a correlation between the spacing of the lamellar surfactant phase in a zinc-triclosan dentifrice and its antiplaque effect (Van der Ouderaa, F. J. and Cummins, D., *Delivery Systems for Agents in Supra- and Sub-gingival Plaque Control*, J. Dent. Res, 68:1617–24. (1989)). However other published human studies have concluded that that there is little benefit from triclosan when used alone or in combination with zinc citrate (Addy, M., Jenkins, S., Newcombe, R., *Toothpastes Containing 0.3% and 0.5% Triclosan (II): Effects of Single Brushings on Salivary Bacterial Counts*, Am. J. Dent. 2:215–19 (1989); Jenkins, S., Addy, H., Newcombe, R., *Toothpastes Containing 0.3% and 0.5% Triclosan (I): Effects on 4–day Plaque Regrowth*, Am. J. Dent. 2:211–214 (1989); Addy, H, Jenkins, S., Newcombe, R., *Studies on the Effect of Toothpaste Rinses on Plaque Regrowth (II): Triclosan With and Without Zinc Citrate Formulations*, J. Clin. Periodontol. 16:385–387 (1989)).

Triclosan is known to be an antibacterial. (See, U.S. Pat. No. 3,629,477 issued Dec. 21, 1971 to Model & Bindlet.) Triclosan has been used in dentifrices. (C.f. Japanese Pat. No. Hei 2-1402, Katsuda et al. published Jan. 5, 1990; U.S. Pat. No. 4,980,153, Jackson et al., issued December 25, 1990; Eur. Pat. Appl. No. 0 161 899, Lane et al., assigned to Unilever, published Nov. 21, 1985; Eur. Pat. Appl. 0 278

744, Caserio et al., assigned to Unilever, published Aug. 17, 1988; Canadian Patent Application 0 961 412, Vinson & Cancro, issued Jan. 21, 1975).

Substituted triclosan compounds have been disclosed in United Kingdom Pat. No. 01 592 011, Reinhardt & Joachim, assigned to Ciba-Geigy AG, published Jul. 1, 1981. The reference teaches that substituted diphenyl ethers are excellent algicides if they contain a group which, on application of the compounds, is able to form the hydroxyl group; the reference discloses as one such compound 2,4,4'-trichloro-2'R-diphenyl ether where R=(HO)$_2$PO—O—. The reference discloses the use of these compounds for the control of algae and the inhibition of algae growth.

Kamat, *Biochemical Aspects of Periodontal Diseases: II. The Possible Significance of Calcium, Phosphorus, and Alkaline Phosphatase in Human Saliva*, 50 J. Indian Dent. Assoc. 171–75 (1978) discloses that alkaline phosphatase in the oral cavity increases with increasing periodontosis severity. See Also, Miglani, et al., *Salivary Phosphatases III: Possible Relation between Salivary Alkaline Phosphatase Activity and Gingival Inflammation*, J. Periodontology, 45(7), 511–13 (1974).

Chemically modifying a drug to convert it into a prodrug is also known. See, Hiller, *A Better Way to Hake the Medicine Go Down*, 253 Science 1095–96 (Sep. 6, 1991).

It is an object of the subject invention to provide oral care compositions comprising certain antibacterial derivatives useful for treating or preventing plaque, gingivitis or periodontal diseases.

It is also an object of the subject invention to provide methods for treating or preventing plaque, gingivitis or periodontal disease.

SUMMARY OF THE INVENTION

The subject invention encompasses compositions for treating or preventing dental plaque, gingivitis or periodontal disease, of the oral cavity in humans or lower animals, comprising a safe and effective amount of an active agent having the structure:

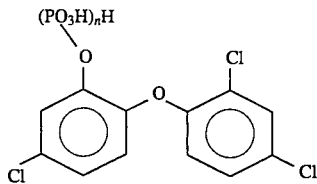

wherein n is an integer from 1 to about 3, or the pharmaceuti-cally-acceptable salts thereof, and a pharmaceutically-acceptable typical oral carrier.

DETAILED DESCRIPTION OF THE INVENTION

The subject invention relates to oral compositions and methods for treating or preventing dental plaque, gingivitis or periodontal disease. The compositions comprise a compound having an Active of the following structure:

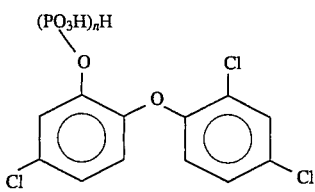

wherein n is an integer from 1 to 3, as the antibacterial agent. In the above structure, n is preferably 1 or 2; more preferably n is 1.

The Actives of the subject invention are anionic, and extremely water soluble (>10%) if a highly purified Active is used. By "highly purified" is meant containing less than about 5% water insoluble impurities or byproducts. While the Actives are extremely water soluble, some methods of manufacture produce undesirable byproducts which may diminish the apparent solubility of the Actives. Preferably, highly purified Actives of the subject invention contain less than about 5% water insoluble impurities, more preferably less than about 3%, most preferably less than about 2% water insoluble impurities.

The Actives of the subject invention are soluble in conventional oral care compositions, such as toothpastes and mouthwashes and are also compatible with components of conventional oral care compositions. Oral care compositions containing such Actives act as a vehicle to deliver triclosan, 2,4,4'-trichloro-2'-hydroxydiphenyl ether, in a bioactive form over a sustained period of time. Specifically, these Actives are prodrug forms of triclosan, a known general antimicrobial.

While the antiplaque activity of the Actives is not limited by the following, it is believed that much activity is at least partially achieved through the mechanisms described hereinbelow. The Actives, being very soluble in water, can diffuse into plaque and bind to phosphatases in saliva, bacterial cell walls and plaque fluid. The Actives can also bind to phosphatases in gingival fluid and gingival lesions. After binding, enzymes process the Actives to generate molecular triclosan. The concentration of triclosan in oral fluids increases until it is bacteriocidal, flattens out for an extended period of time, and eventually falls. A sustained release reservoir for triclosan is thus produced.

The Actives are enzymatically degraded to generate triclosan primarily in the presence of phosphatases. Since the enzymes are primarily located in certain specific sites in the oral cavity, generation of triclosan occurs primarily at these sites. High phosphatase activity has been found in plaque and in certain plaque microorganisms. For example, phosphatase activity has been found in mixed saliva, parotid saliva, submaxillary saliva, gingival lesions, in the wall structures of bacteria, the bacterial cytoplasm, plaque fluid, in oral yeasts such as *Candida albicans*, and in the bacteria on the tongue.

The rate of generation of triclosan from an Active is directly proportional to the local enzymatic activity of phosphatases in that particular site of the oral cavity. For example, individuals with a large amount of plaque, or with active gingivitis have greater local phosphatase activity and will generate more triclosan at these sites from the same dose of Active than will individuals with less plaque or lower gingivitis. Normal oral mucosal epithelium and dental hard tissues have minimal phosphatase activity. Consequently, less triclosan is formed at such sites from Actives of the subject invention, whereas triclosan dosed as itself adsorbs non-specifically on all such lipophilic surfaces.

It is an advantage of the subject invention that oral compositions containing one or more of the Actives are effective in reducing the occurrence of gingivitis without substantial extrinsic development of stain. While not limited by the following, it is believed that the effect occurs by the mechanisms described hereinbelow. The minimum inhibitory concentration (MIC) of an Active in the presence of phosphatase is generally lower for Gram-negative (G−) microorganisms than for Gram-positive (G+) microorganisms. It is believed that this is because G− microorganisms, and in particular some G− gingivitis/periodontal organisms, tend to have high phosphatase activity, whereas G+ microorganisms tend to have lower phosphatase activity. Broad spectrum antimicrobials often have similar MICs for both G+ and G− bacteria. Triclosan, when delivered as triclosan, has an exponential decay curve and is bacteriocidal to G− organisms when at concentrations below its solubility product, hence triclosan is bacteriocidal for a shorter time period than the Actives due to the latter's sustained release mechanism. Staining is unlikely to occur unless the triclosan concentration exceeds the MIC for G+ microorganisms. Therefore, if dosing with one or more of the Actives produces a triclosan concentration profile which exceeds the MIC of G− bacteria but not that of G+ bacteria, gingivitis/periodontal pathogens are eliminated from plaque while avoiding staining.

Compositions

The topical oral carrier for Actives of the subject invention can be any pharmaceutically-acceptable vehicle suitable for use in the oral cavity. Such carriers include the usual components of mouthwashes, toothpastes, tooth powders, prophylaxis pastes, dental solutions, and the like, and are more fully described hereinafter. Dentifrices and mouthwashes are the preferred compositions of the subject invention.

Dentifrice compositions of the subject invention comprise Active, some or all of which is in aqueous solution. Such compositions typically comprise from about 0.001% to about 10% by weight, preferably from about 0.1% to about 5% by weight, and most preferably from about 0.25% to about 2% by weight of Active.

Toothpastes and toothpowders contain as a major component an abrasive. The abrasive polishing materials contemplated for use in the compositions of the subject invention can be any materials which do not excessively abrade dentin. These include, for example, silicas including gels and precipitates, calcium carbonate, dicalcium orthophosphate dihydrate, β-phase calcium pyrophosphate, tricalcium phosphate, calcium polymetaphosphate, insoluble sodium polymetaphosphate, hydrated alumina, and resinous abrasive materials such as particulate condensation products of urea and formaldehyde, and other materials such as those disclosed in Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and pyrophosphates. For these reasons they are preferred for use in the compositions of the subject invention.

The silica abrasive polishing materials useful in the subject compositions, as well as the other abrasives, generally have an average particle size ranging from about 0.1 microns to about 30 microns, preferably from about 5 microns to about 15 microns. The silica abrasive can be precipitated silica or silica gels such as the silica xerogels described in U.S. Pat. No. 3,538,230, issued Mar. 2, 1970 to Pader et al., and in U.S. Pat. No. 3,862,307, issued Jun. 21, 1975, to DiGjulio, both incorporated herein by reference. Preferred are the silica xerogels marketed under the tradename Syloid® by the W. R. Grace & Company, Davidson Chemical Division. Preferred precipitated silica materials include those marketed by the J. H. Huber Corporation under the tradename, Zeodent®, particularly the silica carrying the designation Zeodent 119®. These silica abrasives are described in U.S. Pat. No. 4,340,583, Wason, issued Jul. 20, 1982, incorporated herein by reference.

The total amount of abrasive in the compositions described herein preferably ranges from about 6% to about 70% by weight, more preferably from about 10% to about 50% when the dentifrice is a toothpaste. Higher levels, as high as 90%, may be used if the composition is a tooth powder.

Flavoring agents can also be added to dentifrice compositions to make them more palatable. Suitable flavoring agents include menthol, oil of wintergreen, oil of peppermint, oil of spearmint, oil of sassafras, and oil of clove. Flavoring agents are generally included in the subject compositions in amounts of from about 0% to about 2% by weight, preferably from about 0.04% to about 2%.

Sweetening agents which can be used in the subject dentifrices include aspartame, acesulfame, saccharin, dextrose, levulose and sodium cyclamate. Sweetening agents are generally used in dentifrices at levels of from about 0% to about 3%, preferably from about 0.005% to about 2% by weight.

Coloring agents can also be added to dentifice compositions of the subject invention. Such agents are typically present in amounts of from about 0.001% to about 0.5% by weight.

Dentifrice compositions can also contain surfactants. Suitable surfactants are those which are reasonably stable and foam throughout a wide pH range, including nonsoap anionic, nonionic, zwitterionic and amphoteric organic synthetic detergents. Many suitable surfactants are disclosed in U.S. Pat. No. 4,051,234, issued Sep. 27, 1977, to Gieske et al. and in U.S. Pat. No. 3,959,458 issued to Agricola, Briner, Granger & Widder on May 25, 1976, both of which are incorporated herein by reference. Such surfactants are generally present in the compositions of the subject invention at a level of from about 0% to about 10%, preferably from about 0.2% to about 5%. Surfactants may also be used as solubilizing agents to help retain sparingly soluble components, e.g., some flavoring agents, in solution. Surfactants suitable for this purpose include polysorbates and poloxamers.

In preparing toothpastes, it is necessary to add some thickening material to provide a desirable consistency. Preferred thickening agents are carboxyvinyl polymers, xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from about 0% to about 7%, preferably from about 0.5% to about 5.0% by weight of the total composition, are typical.

It is also desirable to include some humectant material in a toothpaste to keep it from hardening. Suitable humectants include glycerin, sorbitol, and other edible polyhydric alcohols typically at a level of from about 0% to about 80%, preferably from about 5% to about 70% by weight.

Water may also be present in the compositions of the subject invention. Water employed in the preparation of commercially suitable compositions should preferably be deionized and free of organic impurities. Water generally comprises from about 0% to about 60%, preferably from about 10% to about 50%, more preferably from about 20% to about 40%, by weight, of the toothpaste compositions. These amounts of water include the free water which is added plus that which is introduced with other materials, such as with sorbitol.

In addition to the above-described components, the oral compositions of the subject invention may include a number of optional ingredients.

Such optional components of compositions of the subject invention include preservatives. The preservatives prevent microbial growth in the compositions. Suitable preservatives include methylparaben, propylparaben, benzoates and ethanol. If the preservative is ethanol, it generally comprises from 0% to about 35%, preferably from about 5% to about 15%, of the compositions. Other preservatives generally comprise from about 0% to about 5%, preferably from about 0.1% to about 2%, by weight of the compositions.

Other optional ingredients include a safe and effective amount of a fluoride ion source, which typically is in the form of a water-soluble fluoride compound. This water-soluble fluoride compound is typically present in the compositions of the subject invention in an amount sufficient to give a fluoride concentration of from about 0.0025% to about 5.0% by weight, preferably from about 0,005% to about 2.0% by weight. Preferred fluoride sources are sodium fluoride, acidulated phosphate fluoride, and sodium monofluorophosphate. U.S. Pat. No. 3,678,154, issued Jul. 18, 1972 to Widder et al., discloses such salts as well as others, and is incorporated herein by reference.

Other optional ingredients include anticalculus agents, e.g., diphosphonates such as 1-azocycloheptane-2,2-diphosphonate (AHP) and ethane-1-hydroxy-1,1-diphosphonate (EHDP), sodium zinc citrate, phosphocitrate, tripolyphosphate, and linear polycarboxylate (LPC), tetrasodium pyrophosphate, tetrapotassium pyrophosphate, and dihydrogen disodium pyrophosphate, the amount of which typically ranges from about 0% to about 13%, preferably from about 0.1% to about 6% by weight. See, U.S. Pat. No. 4,885,155, Parran & Sakkab, issued Dec. 5, 1989, which is incorporated herein by reference. Pyrophosphates are commonly used anticalculus agents but when incorporated into compositions of the subject invention may diminish the prodrug effect of the Actives somewhat by diverting the oral phosphatases. Preferred anticalculus agents are AHP, EHDP, phosphocitrate, and tripolyphosphates, the latter in combination with LPC.

Another embodiment of the subject invention is liquid compositions, such as mouthwash compositions and dental solutions. For liquid compositions, the concentration of Active typically ranges from about 0.001% to about 10% by weight, preferably from about 0.01% to about 1% by weight, and most preferably from about 0.1% to about 0.5% by weight. Conventional mouthwash composition components can comprise the carrier for the Actives of the subject invention. Mouthwash compositions are typically based on a water/ethanol solution having a ratio of water:ethanol of from about 20:1 to about 2:1. Other ingredients typically found in mouthwash compositions include flavoring agents, sweeteners, humectants and surfactants such as those described above for toothpaste compositions. The humectants, such as glycerin and sorbitol, give a moist feel to the mouth. On a weight basis, the mouthwashes of the subject invention preferably comprise from about 0% to about 60%, more preferably from about 10% to about 25%, ethanol; preferably from 0% to about 50%, more preferably from about 5% to about 20%, humectant as disclosed hereinbefore for dentifrices; preferably from 0% to about 7%, more preferably from about 0.01% to about 0.2%, surfactant as disclosed hereinbefore for dentifrices; prefer ably from 0% to about 3%, more preferably from about 0.005% to about 0.5%, sweetening agent as disclosed hereinbefore for dentifrices such as saccharin; preferably from 0% to about 0.2%, more preferably from about 0.02% to about 0.3%, flavoring agent as disclosed hereinbefore for dentifrices; preferably from about 0.001% to about 0.5% coloring agent; preferably from about 0% to about 5%, more preferably from about 0.1% to about 2%, preservative other than ethanol as disclosed hereinbefore for dentifrices; and the balance water.

Suitable topical dental gels comprise a base of a humectant such as glycerin thickened with a suitable agent. Such gels generally do not contain an abrasive.

Other embodiments of the subject invention include lozenges and chewing gums. Lozenge compositions comprise a lozenge carrier (e.g. a candy base), candy bases being disclosed in, e.g., U.S. Pat. No. 4,472,373 to Ryan, issued Sep. 18, 1984, and in U.S. Pat. No. 4,083,955 to Grabenstetter et al., issued Apr. 11, 1978, both of which are incorporated herein by reference. Chewing gum compositions comprise a chewing gum carrier such as those disclosed in, e.g., U.S. Pat. No. 4,472,373 to Ryan, issued Sep. 18, 1984, and in U.S. Pat. No. 4,083,955 to Grabenstetter et al., issued Apr. 11, 1978, both of which are incorporated herein by reference. Chewing gum carriers may comprise, for example, a gum base, flavoring agents, and sweetening agents; the latter two components have been disclosed hereinbefore for dentifrices.

The pH of the subject compositions and/or their pH in the mouth can be any pH which is safe for the hard and soft tissues of the mouth and is non-hydrolytic. Such pH's are generally from about 3 to about 10, more preferably from about 4 to about 8.5, more preferably still from about 5 to about 7.

Methods of Use

In addition to the above-described oral compositions, the subject invention also encompasses methods of inhibiting plaque and/or calculus on treated tooth surfaces. These methods involve administering a safe and effective amount of the antiplaque Active to the surfaces within the oral cavity. As used herein, "safe and effective amount" means an amount sufficient to induce a significant positive modification in the condition to be treated, but low enough to avoid serious side effects (at a reasonable benefit/risk ratio), within the scope of sound medical judgment. The teeth and other oral cavity tissues are "bathed" in the Active. These methods of the subject invention are typically achieved by administering an oral composition of the subject invention, as described hereinabove, to the oral cavity.

When the oral composition is a toothpaste, typically from about 0.1 grams to about 10 grams, preferably from about 0.25 grams to about 5 grams, more preferably from about 0.5 to about 2 grams of toothpaste is applied to an applicating device, e.g., a toothbrush. The applicating device is then contacted with the oral cavity surfaces in a manner such that the oral composition is contacted with tissue of the oral cavity, especially the teeth and gums. The applicating device may be further used to effect an even distribution of the oral composition onto the tooth surface, for example by brushing. The application preferably lasts for a period of from about 0.5 min. to about 5 min., more preferably from about 1 min. to about 3 min. Application frequency is preferably from about once weekly to about four times daily, more preferably from about three times weekly to about three times daily, more preferably still from about once to about twice daily. Following application, the toothpaste is typically expectorated, and the residue is typically removed from the tooth surface by using a liquid acceptable to the oral cavity, typically water, to rinse the oral cavity followed b) expectoration.

When the oral composition is a mouthwash, typically from about 1 ml. to about 50 ml., preferably from about 5 ml., to about 35 ml., most preferably from about 10 to about 25 ml. of liquid mouthwash containing the antiplaque Active is introduced to the oral cavity. The liquid mouthwash is then agitated for from about 1 second to about 30 minutes, preferably from about 10 seconds to about 5 minutes, more preferably from about 20 seconds to about 2 minutes, within the oral cavity to obtain an improved distribution of the mouthwash over the tissue of the oral cavity. Following agitation, the mouthwash is typically expectorated from the oral cavity.

Active Synthesis

The following is a non-limiting example describing a method of synthesizing an Active of the subject invention, triclosan monophosphate.

A 3-liter, 3-neck round-bottom flask equipped with a mechanical stirrer and an addition funnel is charged with triclosan (200 g), preferably Irgacare MP, HX533, from Ciba-Geigy. Phosphoryl chloride (128 ml) is added and mechanical stirring is begun. After the triclosan is dissolved, the vessel is immersed in an ice-water bath and the solution is stirred for a further 10 minutes. Triethylamine (106 ml) is introduced dropwise via the addition funnel over the course of about 30 minutes. The resulting viscous mixture is stirred for an additional 90 minutes at 0° C., and then for 30 minutes at room temperature.

Diethyl ether (500 ml) is introduced to the reaction flask with stirring, transforming the viscous reaction mixture to a granular suspension. The vessel is again cooled to 0° C. and water (500 ml) is added very slowly, dropwise, over 30 minutes. The dropping rate for the first 100 ml is 1 drop every 2 seconds. The resulting amber, biphasic system which results upon completion of the hydroylsis is stirred at 0° C. for an additional 2 hours, then at ambient temperature overnight.

Diethyl ether (500 ml) is added to the mixture with stirring. The entire contents of the flask is transferred to a separatory funnel. The lower, aqueous phase is drained off and extracted twice with 500 ml portions of diethyl ether. The original ether phase from the reaction mixture is combined with these two subsequent ether extracts. The acidic aqueous phase is discarded.

The ether solution, containing primarily triclosan monophosphate and a phosphodiester by-product, is extracted with 4×1 liter portions of 1N NaOH. The combined NaOH extracts are back extracted with 2×500 ml diethyl ether.

These ether extracts are added to the original ether solution. At this stage, the NaOH solution (pH 12–14) contains pure triclosan monophosphate, while the ether solution contains primarily a phosphodiester by-product, along with traces of unreacted triclosan.

The NaOH solution is acidified with concentrated HCl to pH 1.0±0.2, and is extracted with 3×1 liters of diethyl ether. The combined extracts are dried (MgSO$_4$), filtered, and concentrated in vacuo to an oil. The oil is triturated with dichloromethane (3 liters) which induces crystallization. The resulting white solid is filtered using a Büchner funnel, then dried in vacuo at 25° C. for 24–48 hours. Yield is approximately 255 g of triclosan monophosphate.

ORAL COMPOSITION EXAMPLES

The following non-limiting examples illustrate representative oral compositions containing Actives of the subject invention. The compositions are made using conventional processes.

Example I

The following is a representative example of a toothpaste composition of the subject invention.

| Component | Wt % |
| --- | --- |
| Triclosan diphosphate | 1 |
| Sorbitol | 33 |
| Saccharin | 0.46 |
| Silica | 22 |
| NaF | 0.243 |
| Glycerin | 9 |
| NaOH (50%) | 0.2 |
| Carbopol | 0.2 |
| Keltrol | 0.6 |
| TiO$_2$ | 0.5 |
| Sodium alkyl sulphate (28% soln.) | 4 |
| PEG 6 | 3 |
| FD&C Blue #1 (1% soln) | 0.05 |
| Flavor | 1.1 |
| Water | q.s. |

Example II

The following is a representative toothpaste composition of the subject invention.

| Component | Wt % |
| --- | --- |
| Triclosan monophosphate | 1 |
| Tetrasodium pyrophosphate | 2.05 |
| Tetrapotassium pyrophosphate | 6.272 |
| NaHpyro | 2.1 |
| Sorbitol | 24.9 |
| Saccharin | 0.46 |
| Silica | 22 |
| NaF | 0.243 |
| Glycerin | 9 |
| NaOH (50% Soln.) | 0.2 |
| Carbopol | 0.2 |
| Keltrol | 0.6 |
| TiO$_2$ | 0.5 |
| Sodium alkyl sulphate (28% Soln.) | 4 |
| PEG 6 | 3 |
| FD&C Blue #1 (1% Soln.) | 0.05 |
| Flavor | 1.1 |
| Water | q.s. |

Example III

The following is a representative example of a mouth rinse composition of the subject invention.

| Component | Wt % |
|---|---|
| Triclosan monophosphate | 0.1 |
| EtOH (200 proof) | 16.25 |
| Surfactant (TWEEN 80) | 0.12 |
| Glycerin | 10 |
| Saccharin | 0.06 |
| Flavor | 0.041 |
| F&DC Blue #1 (1% soln) | 0.022 |
| F&DC Yellow #5 (1% soln) | 0.018 |
| Benzoic acid | 0.0045 |
| Sodium Benzoate | 0.054 |
| Water | q.s. |

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A composition for treating or preventing dental plaque, gingivitis or periodontal disease, of the oral cavity in humans or animals, comprising:

(a) from about 0.001% to about 10% by weight of an active agent having the structure:

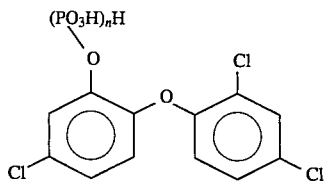

wherein n is an integer from 1 to about 3, or a pharmaceutically-acceptable salt thereof; and (b) a pharmaceutically-acceptable topical oral carrier comprising a flavoring agent or sweetening agent.

2. The composition according to claim 1 wherein the active agent is highly purified.

3. The composition according to claim 2 wherein n is 1.

4. A dentifrice composition for treating or preventing dental plaque, gingivitis or periodontal disease, of the oral cavity in humans or animals, comprising:

a) from about 0.001% to about 10% by weight of an active agent having the structure:

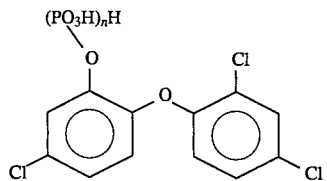

or a pharmaceutically-acceptable salt thereof, wherein n is an integer from 1 to about 3; and b) a pharmaceutically-acceptable topical oral carrier comprising a dental abrasive.

5. The composition according to claim 4 wherein the active agent is highly purified.

6. The composition according to claim 4 wherein n is 1.

7. The composition according to claim 6 wherein the pH of the composition is from about 4 to about 8.5.

8. The composition according to claim 6 wherein the pH of the composition is from about 5 to about 7.

9. The composition according to claim 8 comprising from about 0.1% to about 5% by weight of the active agent.

10. The composition according to claim 9 which additionally comprises a source of fluoride ions yielding from about 0.0025% to about 5% fluoride ions.

11. The composition according to claim 9 which additionally comprises a source of pyrophosphate ions yielding from about 0.1% to about 6% pyrophosphate ions.

12. The composition according to claim 10 which additionally comprises a source of pyrophosphate ions yielding from about 0.1% to about 6% pyrophosphate ions.

13. The composition according to claim 9 which additionally comprises from about 0.1% to about 6% of an anticalculus agent selected from the group consisting of diphosphonates, sodium zinc citrate, phosphocitrate, tripolyphosphate, and linear polycarboxylate.

14. The composition according to claim 10 which additionally comprises from about 0.1% to about 6% of an anticalculus agent selected from the group consisting of diphosphonates, sodium zinc citrate, phosphocitrate, tripolyphosphate, and linear polycarboxylate.

15. A composition selected from the group consisting of a mouthwash, dental solution, and dental gel, for treating or preventing dental plaque, gingivitis or periodontal disease, of the oral cavity in humans or animals, comprising:

a) from about 0.001% to about 10% by weight of an active agent having the structure:

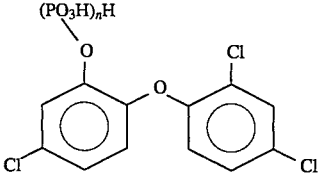

or the pharmaceutically-acceptable salts thereof, wherein n is an integer from 1 to about 3; and b) a pharmaceutical carrier comprising a material selected from the group consisting of ethanol, flavoring agents, and sweetening agents.

16. The composition according to claim 15 wherein n is 1.

17. The composition according to claim 15 wherein the pH of the composition is from about 4 to about 8.5.

18. The composition according to claim 15 wherein the pH of the composition is from about 5 to about 7.

19. The composition according to claim 18 comprising from about 0.01% to about 1% by weight of the active agent.

20. The composition according to claim 19 which additionally comprises a source of fluoride ions yielding from about 0.0025% to about 5% fluoride ions.

21. The composition according to claim 19 which additionally comprises an anticalculus agent.

22. A method for treating or preventing dental plaque, gingivitis or periodontal disease comprising administering to the oral cavity of a human a composition of any of claims 1, 4, 10, 11, 13, 16, 21 and 22.

* * * * *